United States Patent [19]

Strasser

[11] Patent Number: 5,185,011
[45] Date of Patent: Feb. 9, 1993

[54] REUSABLE DIAPER GARMENT

[76] Inventor: Stephanie A. Strasser, 7715 Burthe St., New Orleans, La. 70118

[21] Appl. No.: 722,683

[22] Filed: Jun. 28, 1991

[51] Int. Cl.$^5$ .............................................. A61F 13/15
[52] U.S. Cl. .............................. 604/385.1; 604/385.2
[58] Field of Search ................... 604/373, 378–385.2, 604/386–402, 366, 365; 112/418; 2/78 R, 80, 82, 400, 403, 406, DIG. 5, 278

[56] References Cited

U.S. PATENT DOCUMENTS

| | | | |
|---|---|---|---|
| 2,476,869 | 7/1949 | Hughes | 604/385.1 |
| 2,523,079 | 9/1950 | Walter et al. | 604/398 |
| 2,664,895 | 1/1954 | Shulman | 604/366 |
| 3,090,047 | 5/1963 | Grazia | 2/278 |
| 3,303,515 | 2/1967 | Lash | 2/275 |
| 3,658,063 | 4/1972 | Schaar | 604/385.1 |
| 3,719,189 | 3/1973 | Sherman | 128/287 |
| 3,838,693 | 10/1974 | Sherman | 604/378 |
| 4,397,646 | 8/1983 | Daniels et al. | 604/381 |
| 4,425,128 | 1/1984 | Motomura | 604/384 |
| 4,496,360 | 1/1985 | Joffe et al. | 604/385.1 |
| 4,578,066 | 3/1986 | O'Connor | 604/378 |
| 4,801,298 | 1/1989 | Sorenson et al. | 604/384 |
| 4,900,318 | 2/1990 | Toth | 604/378 |

Primary Examiner—David J. Isabella
Assistant Examiner—K. Reichle
Attorney, Agent, or Firm—Pravel, Gambrell, Hewitt, Kimball & Krieger

[57] ABSTRACT

A reusable multiple layered waterproof diaper garment (11) features an outer layer (25) of garment cloth and is so made and assembled that when fitted to the child and wet by that child's excrement, moisture disposed onto the inner or first layer (55) will not travel through the middle or second layer (35) by way of stitch lines or material layer to expose the outer or third layer (25) to wetness. The middle or second layer (35) is made of waterproof, non-wicking launderable, machine dryable material which is breathable and of such a quality that, when seamed to itself along a separate line of its own surface or when seamed to a surface of a separate piece of similar material, is capable of being seam sealed and rendered liquid impermeable along the seam seal line (36). The first layer (55) is a launderable, machine dryable hypoallerginic cloth and may include multiple layers of such cloth and may include a core (47) of launderable, machine-dryable absorbent material. The hypoallergenic cloth assembly is a diaper pad (45) and the diaper pad (45) is bordered by and sewn to an edging (30, 32, 44, 46) of waterproof, non-wicking, launderable machine-dryable material of such a quality that when the edging material is seamed to itself along a separate line of its own surface or when seamed to a surface of a separate piece of similar material is capable of being seam sealed and rendered liquid impermeable along the seam seal line (36).

1 Claim, 7 Drawing Sheets

REUSABLE DIAPER GARMENT

BACKGROUND OF THE INVENTION

1. Field of the Invention

The present invention relates to reusable children's diapers.

2. General Background of the Invention

Innovations in the field of reusable diapers have targeted improving diaper fit, absorbency, and fastening devices, as well as improving diaper leakage control and waterproofing.

A.

Adjustable fits for the waist and legs have been added to improve variable fit and reduce leakage from soiled or wet diapers. Techniques to improve absorbency include: (1) channel stitching, (2) the inclusion of highly absorbent washable materials such as felt, and (3) diaper construction which allows the garment to secure inserts of a discretionary number of layers of absorbent cloth. U.S. Pat. No. 4,773,906 provides a diaper which offers absorbency while being a diaper that dries relatively quickly considering its degree of absorbency.

Snap fasteners, drawstrings and filament closures are three forms of convenient, diaper closure systems incorporated in diapers to help make diapering easier and safer than that of the traditional diaper pin device. Snap fastener devices are used in U.S. Pat. Nos. 2,242,977, 3,431,908 and 4,397,646.

B.

Leakage control and waterproofing of diapers have also been aims of diaper innovations. Waterproofing is generally achieved by including non-wicking, liquid impermeable material as the outer layer of a multiple layered diaper. reference U.S. Pat. Nos. 2,828,745, 4,196,733, 4,300,563, 4,704,117, 4,801,298.

U.S. Pat. Nos. 3,719,189, 3,838,693 and 4,397,646 are diaper inventions where the layer of waterproof material is an intermediate rather than the outer layer. The inventions include outer layers of cotton blend material, and claim them to be protected from wetness of inner layers. U.S. Pat. Nos. 3,719,189 and 3,838,693, however, are diapers of simple panel work. Neither invention is a diaper garment configured to optimize diaper convenience needs as described above.

U.S. Pat. No. 4,397,646 claims that, due to the construction of the diaper garment, the outer layer, which is typically knit polyester/cotton cloth, will remain dry even if the inner layer is wet. The construction of this invention is such that the inner layer has a soaker layer of felt stitched to it. The felt is sized so it is more narrow than the perimeters of the other layers of the diaper garment. The said perimeters of the other layer are stitched together and include the inner layer of cotton cloth, the waterproof layer, and the outer layer of polyester/cotton knit. The claim is that when the inner layer of cotton is wetted, it will only wick across the inner cotton layer as far as the outer edge of the felt soaker layer. Empirical evidence, however, demonstrates that although the soaker layer does indeed absorb much of the wetness, the liquid dispensed onto the inner layer travels not only through the cloth to the soaker layer, but also wicks across the entire surface of the inner layer. The wetness, upon reaching the perimeter of the inner layer, then travels along the stitching thread (which is used to sew the perimeters of the layers together) and out to the outer layer of polyester/cotton cloth. This liquid is wicked by the cotton blend cloth thus travels across the outer layer of the garment rendering the outer layer wet to a significant degree. The nature of such moisture movement is not unfamiliar to patent discussion in this field as noted by U.S. Pat. No. 4,704,117 on page 4, line 29 : ". . . sewn edges of the diaper . . . are particularly susceptible to wicking moisture . . . ".

SUMMARY OF THE INVENTION

The present invention provides a multiple layered, waterproof, reusable diaper which features an outer layer of garment cloth where, when the diaper garment is fitted to a child, the outer layer of garment cloth is not subject to wetness from the child's excrements caused by seam leakage of thread line induced moisture movement, and is not subject to such wetness caused by physical contact between a wet inner layer and the outer layer garment cloth.

Additionally, this invention to provides such a diaper that:
(1) fits snugly along the legs and waist for a variety of lower body trunk sizes
(2) is absorbent yet dries relatively quickly after being laundered
(3) is convenient to manage when disposing of stool
(4) has convenient non-snagging closure devices
(5) allows for one step diapering, waterproofing and dressing of the child being diapered.

The assembled diaper garment is shaped generally as an hourglass. It has two back and two front laterally extending wings. The inside surface of the outer layer has elastic stitched along the waist back and waist front. This provides a comfortably snug fit for a variety of child waist sizes. Snap fasteners are used for closures. Elastic leg openings are featured to provide a snug fit for a variety of leg sizes and help prevent leakage.

The present invention is constructed with the three following layers: an outer layer which is the third layer of garment cloth, a middle layer which is the second layer of waterproof, non-wicking material, and an inner layer or first layer which is a diaper cloth pad with a waterproof non-wicking border edge.

The third layer of garment cloth serves two functions: (1) of giving an apparel look to the diaper thus permitting the child to look dressed by the diapering procedure, and (2) of giving a soft comfortable feel to the outside of the diaper garment rather than one of a plastic feel, familiar to inventions in this field using liquid impermeable material as the outer layer.

The second layer provides the waterproof layer to the garment. This alone does not guarantee a waterproof diaper as any stitch lines through this layer provide a potential outlet for moisture movement. The second layer however has the novel feature "water-barrier fold" constructed within its frame work to help prevent such moisture movement. This water-barrier fold is a crimp of waterproof material created by seam sealing the material to itself and thereby creating a liquid impermeable seal line and an adjoining crimp of material which is protected from moisture. In this present invention the water-barrier fold is disposed parallel to the leg openings of the diaper garment. This moisture protected crimp is used as a surface with which to stitch the second layer to the third layer along the length of the crimp. This unique feature permits the second layer waterproof material to be secured to the third layer garment cloth at the leg area without exposing the stitch line used to join the two layers to wetness. The second layer also features leg gussets at the leg openings. Elastic strips sewn to the outer perimeters of each leg gusset allow the gussets to snugly cup the child's legs. This feature helps control leakage and serves as a barrier to prevent contact between the first layer diaper pad and the third layer garment cloth.

The first layer is itself a novel feature I call the "Diaper Pad with Waterproof Edging". The pad is made of hypoallergenic washable cloth. This pad may have a core within it made of a washable absorbent material. The pad is sewn only to a waterproof non-wicking edging, and at the edging's inner perimeter. This is done on the pad's four pad wings and along the pad's waist back and waist front. This edging is secured to the other layers at the edging's outer perimeter. The edging is of sufficient width to prevent moisture accumulated along the stitching lines of the inner perimeter from contacting the edge's outer perimeters. The edging on the back wings is sized so that when the waist back wings overlap the waist front wings to allow the snaps to fasten, no diaper pad wetness contacts the outer garment cloth. The snap fastener devices are so incorporated to the garment that they are protected and distanced from moisture.

The first layer's absorbent pad is not secured to the garment along the leg openings. The advantages of this are two fold: (1) without a stitching line common to both the diaper pad and the second layer waterproof material, there can be no moisture movement along any thread of a stitch line which would expose the third layer to wetness; (2) there is the convenience of being able to extend the pad away from of the rest of the garment if pulled, which allows for convenient management of stool disposal, is useful for rinsing and bleaching purposes, and expedites drying time of the diaper garment.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein.

PARTS LIST

The following is a list of suitable parts and materials for the various elements of the preferred embodiment of the present invention.

10—horizontal perimeter of waist back
11—diaper garment
12—horizontal perimeter of waist front
13—crotch area
14—seam lines joining first layer 55, second layer 35 and third layer 25, along vertical perimeter of both left and right laterally extending waist back wings 56 and 57
15—waist back area
16—seam lines joining first layer 55, second layer 35 and third layer 25, along vertical perimeter of both left and right laterally extending waist front wings 66 and 67
17—waist front area
18—left and right leg openings
20—elastic strip secured parallel to perimeter line 10 on inside surface of third layer 25
21—seam lines joining crimp 33 to corresponding cloth flap 26 on both left and right side of diaper garment
22—elastic strip secured parallel to perimeter line 12 on inside surface of third layer 25
25—third layer of diaper garment 11 (outer layer of the diaper cover 111) (preferably cotton blend)
26—cloth flaps
27—seam line joining third layer 25 material to itself to create casings 28 along leg openings 18
28—elasticized casing along leg openings 18
29—elastic strips used in left and right leg casings 28
30—edging strip on waist back 15; part of first layer 55; horizontally disposed along the length of perimeter line 10
31—left and right side leg gussets
32—edging strip of waist front 17; part of first layer 55; horizontally disposed along the length of perimeter line 12
33—crimp of "water-barrier fold"
34—"water-barrier fold"; comprised of crimp 33 and seam line 36
35—second layer of diaper garment 11 (inner layer of the diaper cover 111) (preferably made of Ultrex brand waterproof material)
36—seam seal line of "water-barrier fold"
37—left and right elasticized perimeter along leg openings 18 of second layer 35

38—elastic strips stitched to left and right perimeters 37 of leg openings 18 on second layer 35

44—edging tabs of waist back 15; part of first layer; disposed along vertical perimeters of left and right side wings of hourglass shaped diaper pad 45

45—diaper pad; part of first layer

46—edging tabs of waist front 17; part of first layer; disposed along vertical perimeters of left and right side wings of hourglass shaped diaper pad 45

47—absorbent, launderable core of diaper pad 45

50—seam line joining edging strip 30 to diaper pad 45 and left and right edging tabs 44

51—seam lines joining diaper pad 45 to left and right edging tabs 44

52—seam line joining edging strip 32 to diaper pad 45 and left and right edging tabs 46

53—seam lines joining diaper pad 45 to left and right edging tabs 46

55—first layer of diaper garment 11; "diaper pad with waterproof edging"; comprised of parts 30,32,44,45,46,47.

56—left laterally extending waist back wing

57—right laterally extending waist back wing

60—seam line along horizontal axis of waist back 15 sealing edging 30 to second layer 35 along referenced 60 seam line 62—seam line along horizontal axis of waist front sealing edging 32 to second layer 35 along referenced 62 seam line 66—left laterally extending waist front wing 67—right laterally extending waist front wing 70—seam line along waist back 15 joining first layer 55, second layer 35 and third layer 25 together; disposed parallel to and between perimeter line 10 and seam line 60

72—seam line along waist front 17 joining first layer 55, second layer 35 and third layer 25 together; disposed parallel to and between perimeter line 12 and seam line 62

79—imaginary center line on horizontal axis of diaper garment 11

80—stud portion of snap fastener device

81—prong portion of snap fastener device; fitted to stud 80

82—prong portion of snap fastener device; fitted to socket 83

83—socket portion of snap fastener device

89—imaginary center line on vertical axis of diaper garment 11

111—diaper cover

DETAILED DESCRIPTION OF THE PREFERRED EMBODIMENT

Figure 1:
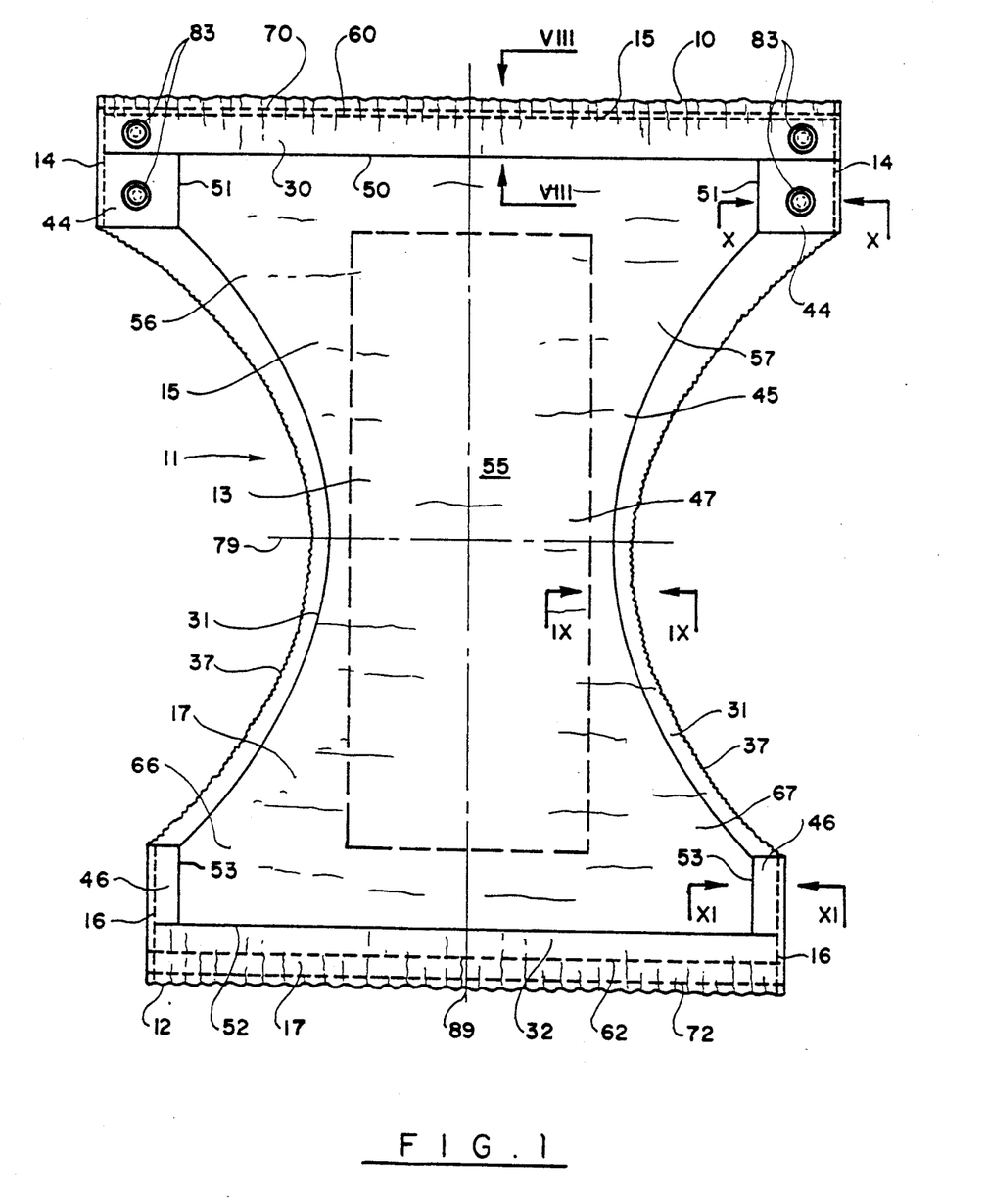
FIG. 1 is a plan view of the inside of the assembled diaper garment of the preferred embodiment of the present invention. When fitted to the child, this side is disposed against the body trunk.
Figure 2:
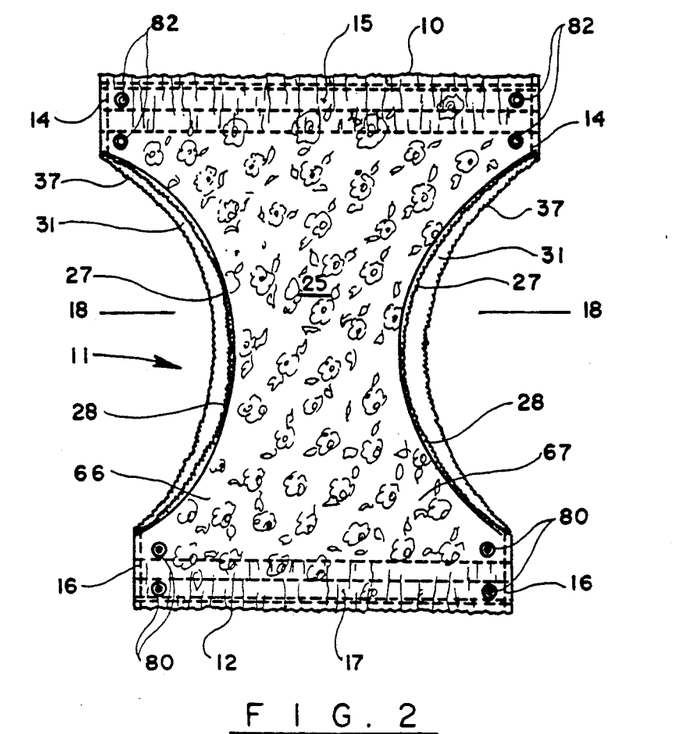
FIG. 2 is a plan view of the outside of the assembled diaper garment of the preferred embodiment of the present invention. When fitted to the child, this side faces away from the body trunk.

As shown in FIGS. 1 and 2 the diaper garment 11 has an hourglass configuration. The distinguishing attributes that make up this hourglass shape serve to define the diaper garment 11 in terms of its waist back 15, waist front 17, crotch area 13, laterally extending wings 56, 57, 66 and 67, and leg openings 18.

As shown in FIG. 1, the center of the diaper garment 11 is determined by the intersection of an imaginary center line 89 on the vertical axis and an imaginary center line 79 on the horizontal axis. Lines 79 and 89 are drawn with broken lines to depict them as imaginary lines. The intersection of these two lines is the center of the diaper garment 11. When the diaper garment 11 is fitted to the child, the area around this point is disposed between the legs of the child. This is the crotch area 13 and is defined by the center third of the diaper garment 11 where the said defining third measurement is taken along the center line on the vertical axis 89 of the diaper garment 11. The oppositely expanding areas from the crotch area 13 to the horizontal perimeter lines 10 and 12 define the areas of the waist back 15 and waist front 17, respectively. Lines 10 and 12 are depicted as ripple lines to show that tautly pulled elastic is stitched to the diaper garment 11 along the waist back 15 and waist front 17. The breadth of the waist back 15 is greater than the same of the waist front 17.

The areas of both the waist back 15 and waist front 17 flare outwardly from the imaginary center line 89 on the vertical axis to form laterally extending wings 56, 57, 66, and 67. The shape and size of the laterally extending waist back wings 56 and 57 correspond to each other. The shape and size of the laterally extending waist front wings 66 and 67 also correspond to each other.

Figure 3:
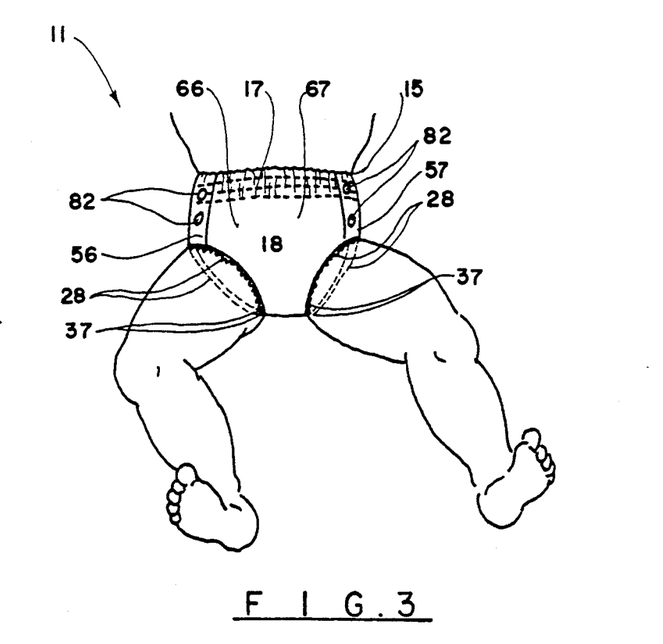
FIG. 3 is a perspective view of the diaper garment of the preferred embodiment of the present invention fitted to the child.

The two perimeters along the outwardly curving area of the hourglass shape of the diaper garment 11 define the two leg openings 18 for each layer of the diaper garment 11. As shown by FIG. 3, when this invention is fitted to the child, the waist back laterally extending wings 56 and 57 overlap the waist front laterally extending wings 66 and 67, and the opposite ends of the outwardly curving perimeters or leg openings 18 meet, encompassing the left and right legs.

The diaper garment 11 is made of three separate hourglass shaped layers. The first layer 55 is the innermost layer. When the diaper garment 11 is fitted to the child the first layer 55 is disposed next to the body trunk. The second layer 35 is the intermediate layer. The third layer 25 is the outermost layer.

Figure 4:
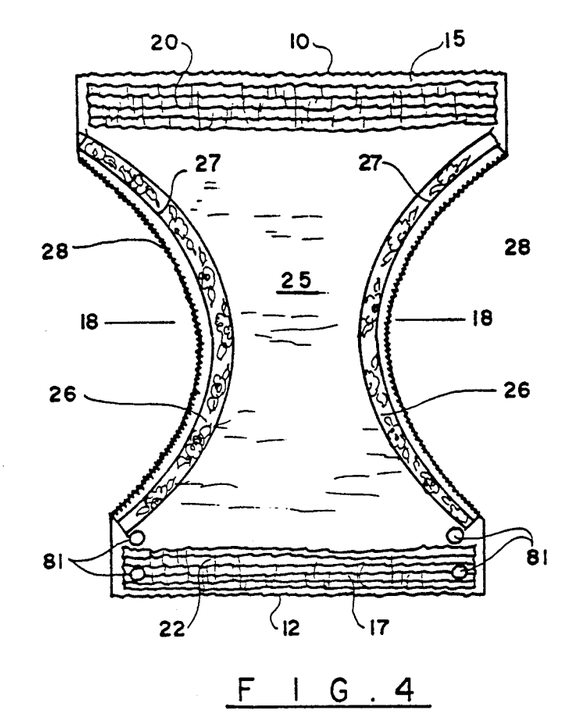
FIG. 4 is a plan view of the inside surface of the third layer.

The third layer 25 may be made of any launderable garment cloth. As shown in FIG. 4, the inside surface of the third layer 25 has elastic strips 20 and 22 secured to it. These elastic strips 20 and 22 run parallel and adjacent to the horizontal perimeter lines 10 and 12 respectively of the diaper garment 11. Elastic strips 20 and 22, in their relaxed state, are of a shorter length than the perimeter lines 10 and 12, respectively. To provide a snug fit for a variety of waist sizes, elastic strips 20 and 22 respectively, are pulled taut to reach a greater extension along each strip's corresponding perimeter line 10 and 12 and each strip is stitched along the horizontal axis of the diaper garment 11.

When the diaper garment 11 is fitted to the child, the casings 28 as shown in FIG. 3 encompass the legs of the child. To create casings 28 a margin of third layer 25 cloth along each leg opening 18 is first folded over to the inside surface of the third layer 25. As shown in FIG. 4, each margin of cloth is then stitched to the third layer 25 along seam line 27 for each leg opening 18. An elastic strip 29 (FIG. 9), which is of a shorter length, in its relaxed state, than the unelasticized leg casing 28 is inserted through each leg casing 28. Each elastic strip 29 is then pulled taut to run a greater length along its respective casing 28. The opposite ends of each elastic strip 29 are then stitched to its respective casing 28 resulting in snugly fitting elastic casings 28 for a variety of leg sizes at each leg opening 18.

A third layer 25 feature I call the "cloth flaps" 26 (shown in FIG. 4) are created during the construction of the casings 28. When the margins of cloth of the third layer 25 are folded over to the inside surface in creating leg casings 28, a wider width of material than needed is folded over to create these casings 28. This leaves a fringe of material, or cloth flaps 26 with a width suitable for additional seam line stitching, along side of the leg casings 28. These cloth flaps 26 serve a function in the assembly of the diaper garment 11.

As shown in FIG. 2, the third layer 25 has snap studs 80 fixed to its outside surface at the laterally extending wings 66 and 67. As shown by FIG. 4, these studs 80 are secured from the inside surface of the third layer 25 and are done so with prongs 81.

Figure 6:
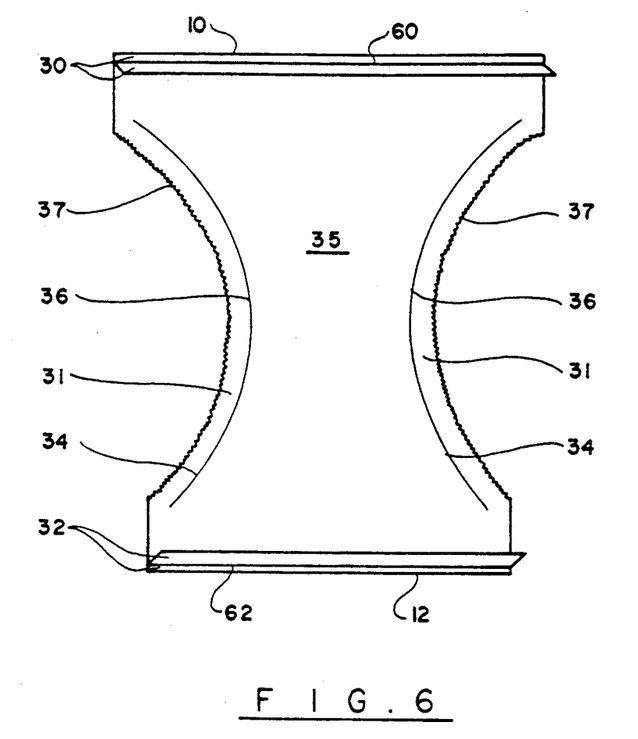
FIG. 6 is a plan view of the inside surface of the second layer, and also shows the waist back and waist front edging strips of the first layer.
Figure 7:
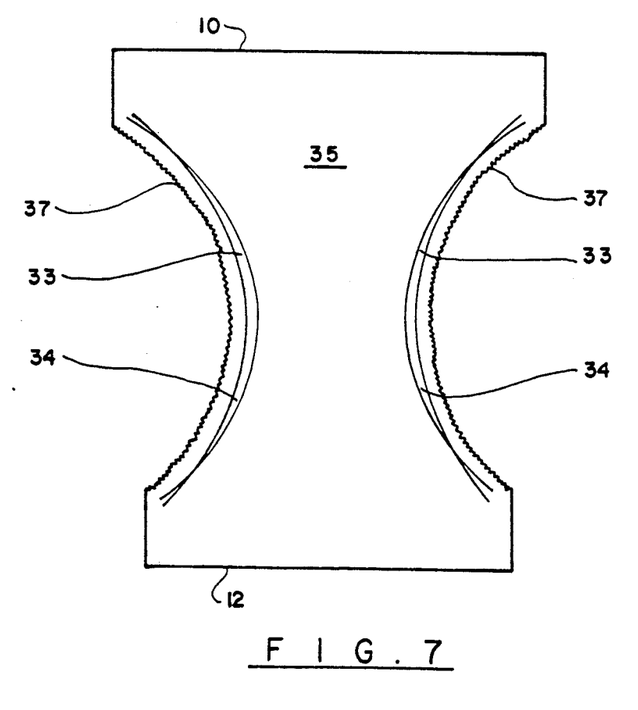
FIG. 7 is a plan view of the outside surface of the second layer.
Figure 9:
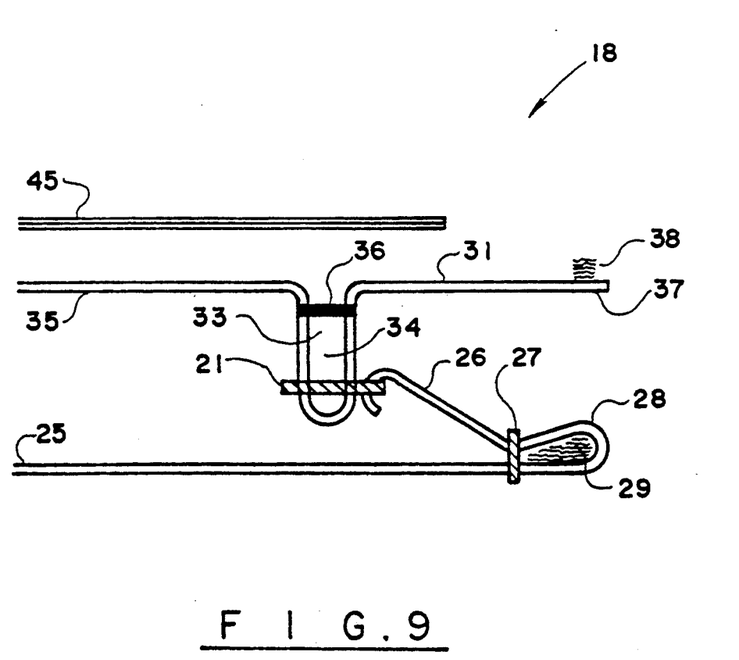
FIG. 9 is a sectional view of the diaper garment of the preferred embodiment of the present invention taken along line IX—IX in FIG. 1.

The second layer 35 is made of launderable, waterproof, non-wicking material. It may be breathable. The size and shape of the second layer 35 is such that when it is assembled as part of this invention, it does not restrict the pull and stretch of the third layer 25 as afforded by the elastic strips 20, 22 and strips 29. A novel feature of this invention I call the "water-barrier fold" 34 (FIG. 9) is constructed as part of and from the material of the second layer 35. The purpose of the water-barrier fold 34 is to provide a surface suitable for stitching the waterproof material of the second layer 35 to the garment material of the third layer 25 without permitting moisture transfer between the two layers 35 and 25 by way of thread line induced moisture movement. To create the water-barrier fold 34 the material of the second layer 35 is pinched together to create a crimp 33 on the outside surface of the third layer 35, (as shown by FIG. 7), and a seam line 36 on the inside surface of the third layer 35, (as shown by FIG. 6). The waterproof material of the second layer 35 is seam sealed along seam line 36 and rendered liquid-impermeable along this line. Crimp 33 is therefore protected from moisture. As shown in FIG. 9, the surface areas of crimp 33 is of sufficient width to accommodate incorporating an additional stitch line.

Seam line 36 need not be a seam sealed line, but may be created by a threaded stitch line. This threaded stitch line is sewn along the same line and for the same length as would be the seal for the seam sealed line 36. The threaded stitch line is sewn along the outside surfaces of the crimp and therefore along the outside surface of the second layer 35. At points along this threaded stitch line where the top thread line and bottom thread line pierce the crimp 33 walls, as is standardly done by sewing machines to form the stitch line, the thread at these points are located on the inside surface of the second layer 35. The source for moisture movement along the thread line is the portion of the thread line that is threaded through the inside surface of the second layer 35. The portion of thread that is exposed to the inside surface of the second layer 35 is a small fraction of the stitch line. As only an insignificant portion of thread line is in contact with moisture, moisture movement is proportionally slower and, as empirical evidence supports, an insignificant amount of moisture is transferred over a long period of time.

Figure 5:
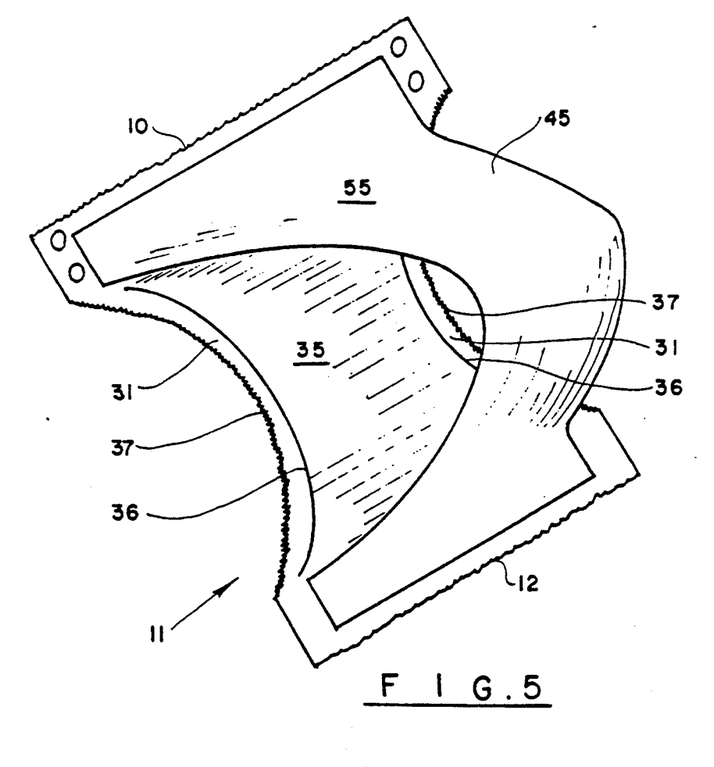
FIG. 5 is a perspective view of the assembled diaper garment of the preferred embodiment of the present invention where the first layer is extended from the remaining layers of the diaper garment.

The second layer 35 also features leg gussets 31. Physical contact and resulting moisture transfer at the perimeters of the leg openings between the first layer diaper pad 45 and the third layer 25 garment material is prevented by the snugly fitted leg gussets 31. As shown in FIG. 9, since the size and shape of the diaper pad 45 is of a more narrow dimension along its leg opening 18 curvature than that of the leg gusset 31 of the second layer 35, and since the elastic perimeters 37 of the gussets 31 snugly cup the legs, the diaper pad 45 is securely retained within the inside surface of the second layer 35. As shown in FIGS. 5 and 6, leg gussets 31 are framed at the leg openings 18 of the second layer 35. The left and right gussets 31 are respectively defined by the boundaries set by the left and right elastic perimeters 37 and the corresponding left and right seam seal line 36 for each leg opening 18. To provide a snug fit at each leg opening 18, a sufficiently tautly pulled strip of elastic 38 is stitched along the entire length of each perimeter defined by line 37. This not only retains the diaper pad 45 within the inside surface of the second layer 35 as described above, it helps retain excrements within the inside surface of the second layer 35. The incorporation of this elastic is depicted by featuring lines 37 as rippled lines.

The first layer 55 is itself a novel feature I call the "Diaper Pad with Waterproof Edging". The size and shape of the first layer 55 is such that when it is assembled as part of this invention, it does not restrict the pull and stretch of the third layer 25 as afforded by the elastic strips 20, 22 and strips 29.

As shown in FIG. 1, the diaper pad 45 portion of the first layer 55 is an hourglass shape. The diaper pad 45 is made of liquid absorbent, launderable, hypoallergenic cloth such as cotton cloth. Sectional views of the diaper pad 45 in FIGS. 8, 9, 10, and 11 show the diaper pad 45 with multiple horizontal lines to illustrate multiple layers. The diaper pad 45 may be of multiple layers of such cloth. As shown in FIG. 1, the diaper pad 45 may have a core 47 of absorbent washable fabric such as additional layers of cotton cloth or felt within its multiple layers of hypoallergenic cloth.

As shown in FIG. 1, diaper pad 45 is partially framed by a waterproof non-wicking edging. This edging is made up of the following parts: edging strip 30, edging strip 32, left and right edging tabs 44 and left and right edging tabs 46. The purpose of including edging strip 30, edging strip 32, left and right edging tabs 44 and left and right edging tabs 46 as part of the first layer 55 is to provide a waterproof non-wicking border material which can be joined to both the diaper pad 45 and the other two layers 35 and 25 of the diaper garment 11 thereby providing a means to secure the diaper pad 45 to the diaper garment 11 while serving the function of isolating moisture of the diaper pad 45 from thread lines which join the first layer 55 to the second layer 35 and the third layer 25. As can be seen in the drawings and understood from the discussion above, the water proof non-wicking edge (edging strip 30, edging strip 32, left and right edging tabs 44 and left and right edging tabs 46) acts as a means for preventing physical contact of the absorbent material 47 of the first layer 55 and the third layer 25 when the diaper garment 11 is worn by a child and also as means for substantially preventing liquid from wicking from the first layer 55 to the third layer 25 through thread-line induced moisture movement, when the diaper garment 11 is worn by the child and the first layer 55 is wet by excrement from the child.

The left and right edging tabs 44 (FIG. 1) are joined to the corresponding left and right vertical perimeters of the laterally extending wings 56 and 57 of the diaper pad 45 by seam lines 51. The left and right edging tabs 46 are joined to the corresponding left and right vertical perimeters of the laterally extending wings 66 and 67 of the diaper pad 45 by seam lines 53.

The edging strips 30 and 32, although being part of the first layer 55, may be made of material extending from the material of the second layer 35. Before assembly, as shown in FIG. 6, material from the second layer 35 is folded down and in to the inside surface of the second layer 35. The fold lines conform to the perimeter lines 10 and 12 of the assembled diaper garment 11. The folded-over portions of material become part of the first layer 55 and are designated as edging strip 30 for the edging strip along the waist back 15 and edging strip 32 for the edging strip along the waist front 17. As shown in FIG. 1, the edging strip 30 is joined to the waist back 15 of the diaper pad 45 by seam line 50. Seam line 50 also joins left and right tabs 44 to edging strip 30. As shown in FIG. 1, edging strip 32 is joined to the waist front 17 of the diaper pad 45 by seam line 52. Seam line 52 also joins left and right tabs 46 to edging strip 32. Both seam line 50 and 52 end short of reaching the vertical perimeters of wings 56 and 57 and wings 66 and 67 respectively. This is to physically separate moisture-carrying seam lines 50 and 52 from seam lines 14 and 16 which must remain dry as they are used to assemble the three layers 55, 35 and 25 at the vertical perimeters of the wings 56, 57, 66 and 67.

Stitch line 50 may instead intersect stitch lines 14, and stitch line 52 may intersect stitch lines 16. The amounts of moisture movement permitted by the four cross points at the above intersections is insignificant.

Figure 8:
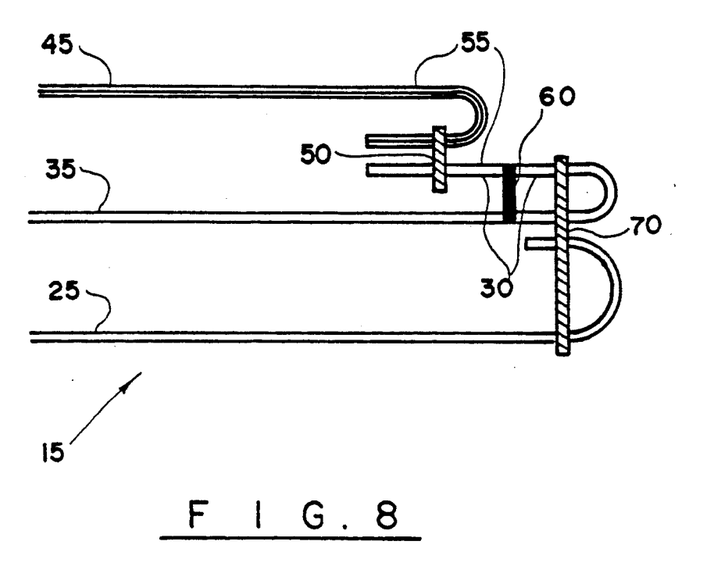
FIG. 8 is a sectional view of the diaper garment of the preferred embodiment of the present invention taken along line VIII—VIII in FIG. 1.

In addition to the preparation of each layer, the assembly of the three layers 55, 35 and 25 is achieved in such a manner to prevent wetness of the diaper pad 45 from passing through the second layer 35 to reach the third layer 25. FIG. 8 shows how the waist back 15 is assembled so the three layers 55, 35 and 25 are joined without allowing thread line moisture movement. The following discussion of the assembly applies to both the waist back 15 and waist front 17. As shown in FIG. 8, diaper pad 45 is joined to the edging strip 30 by seam line 50. Because edging strip 30 is non-wicking and waterproof, however, moisture from the diaper pad 45 or seam line 50 will not wick across or through edging strip 30 to expose seam lines 60 or 70 to moisture. Although diaper pad 45 is not joined to the second layer 35 it rests on it and thus exposes the inside surface of the second layer 35 to moisture. Because the second layer 35 is non-wicking and waterproof however, it will not pull moisture beyond the perimeter lines of diaper pad 45. As shown by FIG. 5 however, the diaper pad 45 is able to shift out of true along the longitudinal axis. This is because the diaper pad 45 is not secured to the diaper garment 11 along the longitudinal axis at the leg openings 18. Because of this ability to shift out of true, seam line 60, and its waist front 17 corresponding seam line 62 is subject to diaper pad 45 wetness should the diaper pad 45 be shifted from its true position when put on the child. Line 60, as shown in FIG. 8, and the corresponding waist front line 62, however, are liquid-impermeable seam sealed lines that prevent any wetness on diaper pad 45, any wetness accumulated on seam lines 50 and 52 that join the diaper pad 45 to the edging strips 30 and 32, or any wetness on the second layer 35 from contacting seam line 70 or 72 respectively. This is critical because it is seam lines 70 and 72 which secure the garment material of the third layer 25 to the first and second layers 55 and 35 along the waist and therefore must remain dry.

Seam sealed lines 60 and 62 can instead be threaded stitch lines. As threaded stitch lines they also form a boundary by which the diaper pad 45 cannot push past, and thus they also prevent physical contact between the diaper pad 45 and stitch lines 70 and 72. As threaded stitch lines they are sewn along the same lines and for the same lengths as would be the seal for the seam sealed lines 60 and 62. These threaded stitch lines are sewn along the outside surfaces of the crimp and therefore along the outside surface of the second layer 35 and the inside surface of first layer 55. At points along this threaded stitch line where the top thread line and bottom thread line pierce the first and second layers 55 and 35, as is standardly done by sewing machines to form the stitch line in joining the two layers together, the thread at these points is located on the inside surface of the second layer 35. The source for moisture movement along these thread lines is the portion of the thread line that is threaded through the inside surface of the second layer 35. The portion of thread that is exposed to the inside surface of the second layer 35 is a small fraction of the stitch line. As only an insignificant portion of thread line is in contact with moisture, moisture movement is proportionally slower and, as empirical evidence supports, an insignificant amount of moisture is transferred over a long period of time.

FIG. 9 shows how the water-barrier fold 34 permits the joining of the second and third layers 35 and 25 along the leg openings 18 of each layer 35 and 25 without allowing moisture on the diaper pad 45 or inside surface of the second layer 35 to reach the third layer 25 garment cloth. As shown in FIG. 9, seam line 21 joins the cloth flap 26 of the third layer 25 to the moisture protected surface area afforded by the crimp 33 of the second layer 35. The liquid-impermeable seal line 36 prevents the wetness of diaper pad 45 or a wet inside surface of the second layer 35 from reaching the thread of seam line 21. By this arrangement, the diaper garment 11 is integrally joined at the leg openings 18, and no thread line moisture movement can be transferred to the garment cloth of the third layer 25 by the thread line of seam line 21.

The diaper pad 45 is not stitched to the other layers 35 and 25 in the above assembly including the water-barrier fold 34 because it is neither necessary nor desirable to do so. Should the diaper pad 45 and the second layer 35 be sewn together, the thread line used to secure the diaper pad 45 and second layer 35 would need to thread through the diaper pad 45 as well as both the inside surface and outside surface material of the second layer 35. This would be a deficient feature, because such a thread line, being threaded through the diaper pad 45, would carry moisture along that thread line to the outside surface of the second layer 35, and thus expose the third layer 25 to moisture. The third layer 25 would pull that moisture from such a thread line across its surface and would be rendered wet to a significant degree. Precautions could be taken by way of securing the diaper pad 45 to a type of water-barrier fold created on the inside surface of the second layer 35. However, such measures are unnecessary because (1) it does not harm the integrity of the garment to have the diaper pad 45 free floating along the center curvature lines of the diaper garment 11, and (2) it is useful to have the diaper pad 45 free floating at this region. Although clearly incidental to preventing seam leakage, the added utility of this free floating diaper pad 45 along the center curvature lines is twofold. Firstly, it allows for faster drying time because heat in the dryer can circulate on both sides of the diaper pad 45. Secondly, the diaper pad 45 can be extended away from the second and third layers 35 and 25 at the diaper pad 45 region. This is useful for the purpose of dumping stool conveniently in the toilet and for allowing flushing water to force stool off the pad. Also, the principle of extending the diaper pad 45 away is useful for rinsing the diaper pad 45 portion in rinse solutions such as chlorine bleach solutions, which are harmful to garment cloth, most synthetic materials used as waterproof materials in washable diaper garments and to elastic materials. Although the feature of the diaper pad's 45 ability to flap in the dryer machine, thus facilitating faster drying, is shared with U.S. Pat. No. 4,773,906, my invention's purpose of not stitching along the leg opening curvatures, is to prevent thread line seam leakage. The benefits described above which go beyond the utility of seam leakage control are above and beyond the present invention's main purpose.

Figure 10:
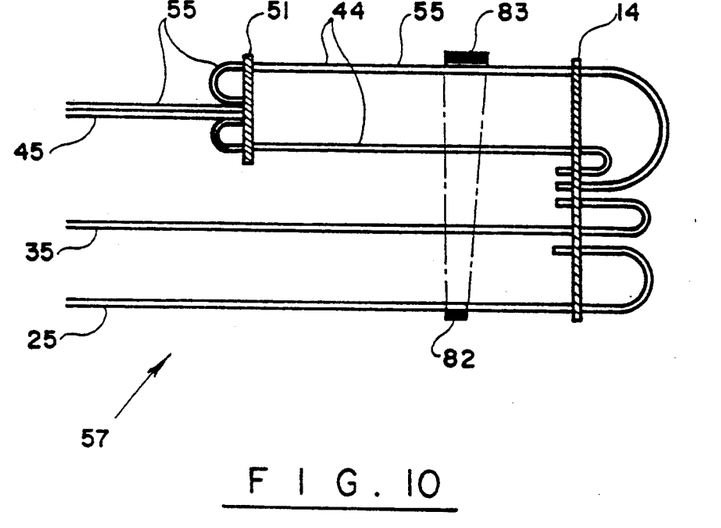
FIG. 10 is a sectional view of the diaper garment of the preferred embodiment of the present invention taken along line X—X in FIG. 1.
Figure 11:
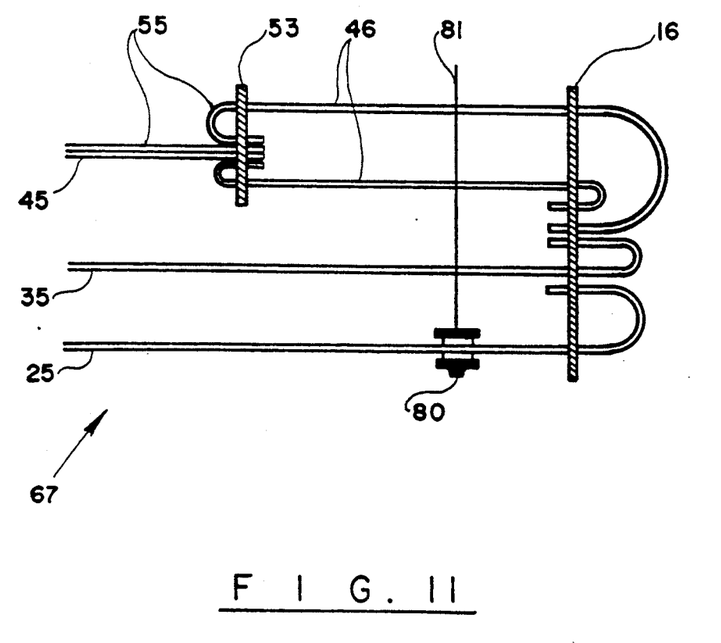
FIG. 11 is a sectional view of the diaper garment of the preferred embodiment of the present invention taken along line XI—XI in FIG. 1.
Figure 12:
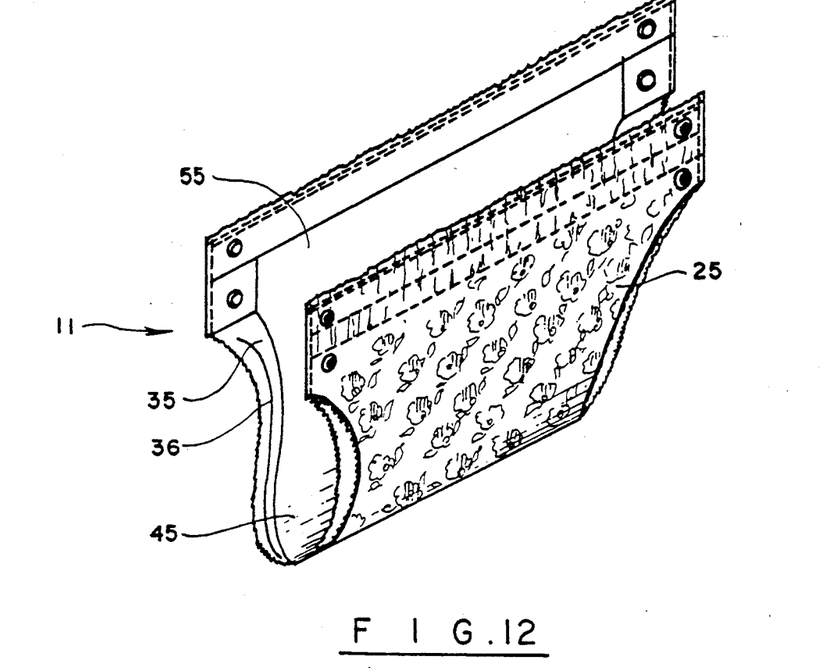
FIG. 12 is a perspective view of the three layers of the diaper garment of the preferred embodiment of the present invention.

The layers 55, 35 and 25 are joined along the perimeters of the vertical axes of each wing 56, 57, 66 and 67. As shown in the sectional views of FIGS. 10 and 11, it is along seam lines 14 and 16 that all three layers 55, 35 and 25 are joined by a common thread line. Because thread lines can serve as conduits for moisture movement, seam lines 14 and seam lines 16 are all physically separated from the diaper pad 45. The first layer edging strip 30 and edging tabs 44, and edging strip 32 and edging tabs 46 serve as physical border areas against moisture movement. As shown in FIG. 10, moisture accumulated at stitch line 51 cannot travel across or through the non-wicking, waterproof edging tabs 44 to transfer moisture from seam line 51 or diaper pad 45 to either the sockets 83 or thread of seam line 14. As shown in FIG. 11, moisture accumulated at stitch line 53 cannot travel across or through the non-wicking, waterproof edging tabs 46 to transfer moisture from seam line 53 or diaper pad 45 to the thread of seam line 16.

As can be seen in FIGS. 1 and 2, the perimeter of third layer 25 is laterally spaced from the perimeter of the absorbent material (diaper pad 45) by a waterproof area comprising waterproof gussets 31, waterproof edging strips 30 and 32, and waterproof edging tabs 44 and 46.

Left and right edging tabs 44 have sockets 83 fixed through the edging tabs 44. Sockets 83 are fastened to the edging tabs 44 by prongs 82. The prongs 82 may pierce the second and third layers 35 and 25 of the diaper garment 11. The size and shape of edging tabs 44 at the laterally extending wings 56 and 57 are of sufficient width, and the sockets 83 and prongs 82 are so positioned on the wings 56 and 57 that when the diaper garment 11 is fitted to the child, and the wings 56 and 57 overlap the wings 66 and 67 to fasten the sockets 83 to the studs 80 no part of the diaper pad 45 contacts the third layer 25 garment cloth. If there were to be contact, then moisture would wick from diaper pad 45 across the third layer 25 and render the outer layer of the diaper garment 11 wet.

Instead of snap devices, hook and pile type device closures such as Velcro ® brand hook-and-loop fasteners can be used. The hook portion of the device may be fixed to the outside surface of the third layer 25 along the waist front 17. The pile portion of the device may be fixed to the tabs 44 or act as a portion of the tabs 44. The size and shape of the hook portion and the size and shape of the pile portion of the hook and pile type device in combination with the size and shape of tabs 44 must be coordinated to accommodate overlap by the waist back wings 56 and 57 while preventing diaper pad 45 from contacting the third layer 25 when the diaper garment 11 is fitted to the child at any of the chosen fits afforded by the hook and pile closure device.

Figure 13:
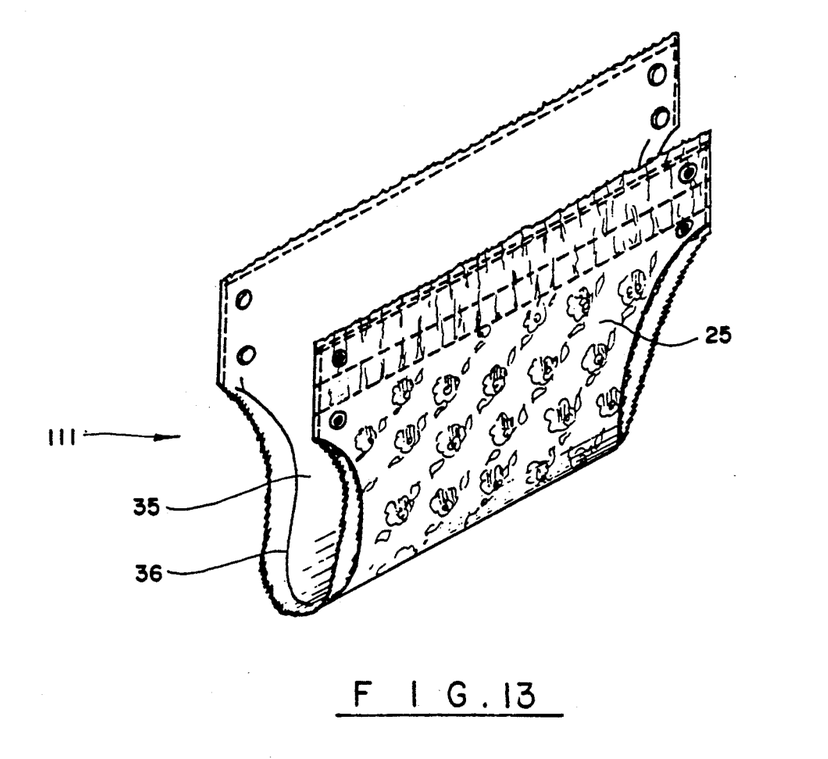
FIG. 13 is a perspective view of the two layers of the diaper cover of an alternative embodiment of the present invention.

A second embodiment of the present invention is the diaper cover 111 and is shown in FIG. 13. The diaper cover 111 is the same as the diaper garment 11 except that the first layer 55 is omitted. Diaper cover 111 can be used to cover conventional diapers.

The foregoing embodiments are presented by way of example only; the scope of the present invention is to be limited only by the following claims.

What is claimed as invention is:

1. A reusable multiple-layered waterproof diaper garment comprising:
   (a) a first, innermost layer comprising absorbent, launderable, machine-dryable material;
   (b) a second, middle layer comprising waterproof, non-wicking, launderable, machine-dryable material attached to the first, inner layer;
   (c) a third, outer layer comprising launderable, machine-dryable garment cloth;
   (d) fastening means for fastening the diaper garment on a child;
   (e) contact-preventing means for preventing physical contact of the absorbent material of the first layer and the third layer when the diaper garment is worn by a child;
   (f) wicking-preventing means for substantially preventing liquid from wicking from the first layer to the third layer through stitch-line induced moisture movement, when the diaper garment is worn by the child and the first layer is wet by excrement from the child; and
   (g) at least said second and third layers each having two leg openings, wherein:
   (i) the second layer has an outer surface;
   (ii) the second layer, at predetermined locations including at least adjacent said leg spacing is seamed to its own surface generating a crimp of moisture-protected material on the outer surface of the second layer and that the crimp of moisture-protected material is of sufficient width to accommodate a stitching line, the moisture-protected material forming part of the wicking-preventing means; and
   (iii) the third layer at each leg opening, is stitched to the corresponding crimp of moisture-protected material on the outer surface of the second layer adjacent the leg openings.

* * * * *